(12) United States Patent
Nakamura et al.

(10) Patent No.: US 10,723,679 B2
(45) Date of Patent: *Jul. 28, 2020

(54) METHOD FOR PRODUCING (Z)-1-CHLORO-2,3,3-TRIFLUORO-1-PROPENE

(71) Applicant: AGC Inc., Chiyoda-ku (JP)

(72) Inventors: Masahiko Nakamura, Chiyoda-ku (JP); Atsushi Fujimori, Chiyoda-ku (JP); Mari Ichinokawa, Chiyoda-ku (JP); Hidekazu Okamoto, Chiyoda-ku (JP); Hiroaki Mitsuoka, Chiyoda-ku (JP)

(73) Assignee: AGC Inc., Chiyoda-ku (JP)

(*) Notice: Subject to any disclaimer, the term of this patent is extended or adjusted under 35 U.S.C. 154(b) by 0 days.

This patent is subject to a terminal disclaimer.

(21) Appl. No.: 16/592,901

(22) Filed: Oct. 4, 2019

(65) Prior Publication Data

US 2020/0031744 A1     Jan. 30, 2020

Related U.S. Application Data

(63) Continuation of application No. 16/422,406, filed on May 24, 2019, now Pat. No. 10,472,307, which is a continuation of application No. PCT/JP2017/042462, filed on Nov. 27, 2017.

(30) Foreign Application Priority Data

Nov. 28, 2016   (JP) .................. 2016-229919

(51) Int. Cl.
C07C 17/383  (2006.01)
C07C 17/25   (2006.01)
C07C 21/18   (2006.01)

(52) U.S. Cl.
CPC ............ *C07C 17/383* (2013.01); *C07C 17/25* (2013.01); *C07C 21/18* (2013.01)

(58) Field of Classification Search
CPC ....... C07C 17/383; C07C 17/25; C09K 5/044; C09K 5/045; C09K 2205/126; C09K 2205/32

See application file for complete search history.

(56) References Cited

U.S. PATENT DOCUMENTS

| 5,629,461 | A | 5/1997 | Yasushi et al. |
| 2011/0275723 | A1 | 11/2011 | Hulse et al. |
| 2014/0234517 | A1 | 9/2014 | Hulse et al. |
| 2015/0231527 | A1 | 9/2015 | Singh |
| 2018/0162794 | A1 | 6/2018 | Ichinokawa et al. |

FOREIGN PATENT DOCUMENTS

| JP | 2013-525486 | 6/2013 |
| JP | 2016-29174  | 3/2016 |
| JP | 2016-160233 | 9/2016 |
| JP | 2016-164152 | 9/2016 |
| WO | WO 94/14737 | 7/1994 |

OTHER PUBLICATIONS

International Search Report dated Jan. 9, 2018 in PCT/JP2017/042462 filed Nov. 27, 2017 (with English Translation).
Written Opinion dated Jan. 9, 2018 in PCT/JP2017/042462 filed Nov. 27, 2017.

*Primary Examiner* — Jafar F Parsa
(74) *Attorney, Agent, or Firm* — Oblon, McClelland, Maier & Neustadt, L.L.P.

(57) ABSTRACT

Provided is a method for producing (Z)-1-chloro-2,3,3-trifluoro-1-propene where (E)-1-chloro-2,3,3-trifluoro-1-propene and water can be efficiently removed and (Z)-1-chloro-2,3,3-trifluoro-1-propene with higher purity can be obtained at a higher recovery ratio. The method for producing (Z)-1-chloro-2,3,3-trifluoro-1-propene includes: distilling a distillation composition which contains (Z)-1-chloro-2,3,3-trifluoro-1-propene, (E)-1-chloro-2,3,3-trifluoro-1-propene and water to remove (E)-1-chloro-2,3,3-trifluoro-1-propene and water as an azeotropic composition or an azeotropic-like composition.

5 Claims, 1 Drawing Sheet

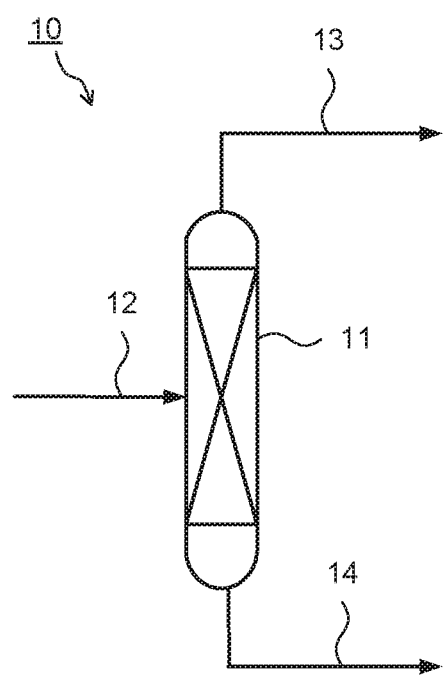

METHOD FOR PRODUCING (Z)-1-CHLORO-2,3,3-TRIFLUORO-1-PROPENE

CROSS-REFERENCE TO RELATED APPLICATIONS

This application is a continuation of U.S. application Ser. No. 16/422,406, filed on May 24, 2019, which is a continuation of prior International Application No. PCT/JP2017/042462 filed on Nov. 27, 2017, which is based upon and claims the benefit of priority from Japanese Patent Application No. 2016-229919 filed on Nov. 28, 2016; the entire contents of all of which are incorporated herein by reference.

FIELD

The present invention relates to a method for producing (Z)-1-chloro-2,3,3-trifluoro-1-propene.

BACKGROUND

It is planned that production of hydrochlorofluorocarbon (HCFC) is regulated due to its adverse effect on the ozone layer. Examples of HCFC include 3,3-dichloro-1,1,1,2,2-pentafluoropropane (HCFC-225ca), 1,3-dichloro-1,1,2,2,3-pentafluoropropane (HCFC-225cb), and so on. Development of a compound alternative thereto is demanded in accordance with the regulation of HCFC.

An example of the compound alternative to HCFC includes, for example, 1-chloro-2,3,3-trifluoropropene (HCFO-1233yd). HCFO-1233yd has a small global warming potential (GWP) and can be suitably used for uses in a cleaning agent, a solvent, a refrigerant, a foaming agent, aerosol, and so on.

There are a Z-isomer of HCFO-1233yd (HCFO-1233yd(Z)) and an E-isomer of HCFO-1233yd (HCFO-1233yd(E)) being structural isomers in HCFO-1233yd. HCFO-1233yd(Z) is mainly used for the uses in the cleaning agent, the solvent, the refrigerant, the foaming agent, and the aerosol.

International Publication No. 1994/14737 discloses a method for producing 1,1,2,2,3-pentafluoropropane (HCFC-245ca) from 1-chloro-2,2,3,3-tetrafluoropropane (HCFC-244ca) and hydrogen fluoride. Since HCFO-1233yd is secondary produced through this method, a composition containing HCFO-1233yd is obtained by separating HCFO-1233yd from a composition obtained by the above-stated method.

Though HCFO-1233yd generated by the above method is a mixture of HCFO-1233yd(E) and HCFO-1233yd(Z), it is preferable that each of HCFO-1233yd(Z) and HCFO-1233yd(E) can be used independently, and a composition of the mixture is adjustable depending on uses. However, International Publication No. 1994/14737 does not describe separation of HCFO-1233yd(E) and HCFO-1233yd(Z), and adjustment of the composition.

There is a case when water is mixed in during a production process of HCFO-1233yd. When water (moisture) is contained in the composition containing HCFO-1233yd(Z), reliability and performance may deteriorate when it is used as the cleaning agent, the solvent, the refrigerant, the foaming agent, or the aerosol to cause various problems. A content of water is preferably reduced as much as possible in order to avoid such an unfavorable influence.

In general, a by-product is removed from a reaction product through distillation by using a boiling point difference therebetween, but boiling points are close to one another such that the boiling point of HCFO-1233yd(Z) is about 54° C. and the boiling point of HCFO-1233yd(E) is about 48° C., It is therefore difficult to separate by means of a normal distillation column, and a method to more efficiently remove HCFO-1233yd(E) has been demanded.

Further, separation by means of distillation is difficult because a mixture of HCFO-1233yd(Z) and water forms an azeotropic-like composition, and a method to efficiently remove water has been demanded.

SUMMARY

The present invention is made to solve the above-stated problems, and an object thereof is to provide a method for producing HCFO-1233yd(Z) where HCFO-1233yd(E) and water are efficiently removed from a composition containing HCFO-1233yd(Z), HCFO-1233yd(E) and water, and a recovery ratio of HCFO-1233yd(Z) is high, and purity of HCFO-1233yd(Z) can be increased.

The present invention provides a method for producing HCFO-1233yd(Z) having a composition described below.

[1] A method for producing HCFO-1233yd(Z) characterized in that distilling a distillation composition containing HCFO-1233yd(Z), HCFO-1233yd(E) and water to remove HCFO-1233yd(E) and water as an azeotropic composition or an azeotropic-like composition.

[2] The method for producing HCFO-1233yd(Z) according to [1], wherein a content ratio of water with respect to a sum total of a content of HCFO-1233yd(E) and a content of water is 0.001 to 5 mass % in the distillation composition.

[3] The method for producing HCFO-1233yd(Z) according to [1] or [2], wherein the distillation composition is prepared by adding HCFO-1233yd(E) to a composition containing HCFO-1233yd(Z) and water.

[4] The method for producing HCFO-1233yd(Z) according to [1] or [2], wherein the distillation composition is prepared by adding water to a composition containing HCFO-1233yd(Z) and HCFO-1233yd(E).

[5] The method for producing HCFO-1233yd(Z) according to any one of [1] to [4], wherein the distillation composition is prepared by using a reaction composition containing HCFO-1233yd(Z) obtained by subjecting HCFC-244ca to a dehydrofluorination reaction.

[6] The method for producing HCFO-1233yd(Z) according to any one of [1] to [5], wherein the distillation is carried out by a distillation column whose column top temperature is set to 40 to 55° C.

According to the method for producing HCFO-1233yd(Z) of the present invention, HCFO-1233yd(E) and water can be efficiently removed from a composition containing HCFO-1233yd(Z), HCFO-233yd(E) and water, a recovery ratio of HCFO-1233yd(Z) can be increased, and purity of HCFO-1233yd(Z) can be increased.

BRIEF DESCRIPTION OF THE DRAWINGS

FIG. 1 is a view illustrating an example of a distillation apparatus used for a production method according to an embodiment.

DETAILED DESCRIPTION

In this specification, 1-chloro-2,3,3-trifluoropropene (HCFO-1233yd) is also just called "1233yd". Further, a Z-isomer of HCFO-1233yd being a structural isomer of HCFO-1233yd is also just called "1233yd(Z)", and an E-isomer of HCFO-1233yd is also just called "1233yd(E)".

In this specification, as for halogenated hydrocarbon, when an abbreviated name of a compound is given in a parenthesis after a compound name, the abbreviated name is used instead of the compound name according to need. As for a compound having a double bond in a molecule and having an E-isomer and a Z-isomer, the E-isomer and the Z-isomer are respectively represented by (E) or (Z) given at the end of the abbreviated name of the compound name. The compound name without (E) or (Z) at the end represents that the compound is any of the (E) isomer, the (Z) isomer, or a mixture of the (E) isomer and the (Z) isomer.

Hereinafter, embodiments of the present invention are explained.

A method for producing 1233yd(Z) according to the present embodiment is characterized in that distilling a distillation composition containing 1233yd(Z), 1233yd(E) and water to remove 1233yd(E) and water from the distillation composition as an azeotropic composition or an azeotropic-like composition. Here, a part or all of the azeotropic composition or the azeotropic-like composition of 1233yd(E) and water may be removed.

First, the azeotropic composition and the azeotropic-like composition are explained.

In general, the azeotropic composition is defined as one where a composition of a gas phase generated by gasification of a liquid phase becomes the same as a composition of the liquid phase, or a composition of a liquid phase generated by liquefaction of a gas phase becomes the same as a composition of the gas phase in a mixture. The azeotropic composition can be suitably used for distillation and reflux because a composition thereof does not change through evaporation and condensation. The composition of the azeotropic composition changes depending on pressure conditions.

Meanwhile, the azeotropic-like composition exhibits similar behavior as the azeotropic composition. That is, in the azeotropic-like composition, a composition of a gas phase generated by gasification of a liquid phase becomes almost the same as a composition of the liquid phase, or a composition of a liquid phase generated by liquefaction of a gas phase becomes almost the same as a composition of the gas phase. The azeotropic-like composition can be suitably used for distillation and reflux as same as the azeotropic composition because a composition thereof does not change through evaporation and condensation.

The present inventors found that 1233yd(E) and water formed an azeotropic composition or an azeotropic-like composition. Further, the present inventors found that the azeotropic composition or the azeotropic-like composition of 1233yd(E) and water was formed in preference to an azeotropic composition or an azeotropic-like composition of 1233yd(Z) and water.

The azeotropic composition or the azeotropic-like composition of 1233yd(E) and water has a lower boiling point compared to 1233yd(Z). That is, the boiling point of 1233yd (Z) is about 54° C., where the boiling point of the azeotropic composition or the azeotropic-like composition of 1233yd (E) and water is about 40 to 48° C. The boiling point is a boiling point under atmospheric pressure. The atmospheric pressure is 101.325 kPa.

Accordingly, it is possible to separate 1233yd(Z) from 1233yd(E) and water by using the azeotropic composition or the azeotropic-like composition of 1233yd(E) and water. It is thereby possible to efficiently remove 1233yd(E) and water from the distillation composition, increase a recovery ratio of 1233yd(Z), and increase purity of 1233yd(Z).

The azeotropic composition of 1233yd(E) and water has a relative volatility represented by the following expression (1) under atmospheric pressure to be 1.00, and the azeotropic-like composition of 1233yd(E) and water has a relative volatility represented by the following expression (1) to be in a range of 1.00-0.20. Almost the same effect as the azeotropic composition can be obtained if the azeotropic-like composition has the relative volatility in the above-stated range.

Relative volatility=(mol % of water in gas phase/mol % of 1233yd(E) in gas phase)/(mol % of water in liquid phase/mol % of 1233yd(E) in liquid phase) (1)

A composition range capable of obtaining a desired relative volatility can be found as described below. First, the composition of the mixture of 1233yd(E) and water is gradually changed to measure the compositions of the liquid phase and the gas phase by using a Karl Fischer moisture meter and a gas chromatograph. The relative volatility is calculated from the above-stated expression (1) by using the compositions of the liquid phase and the gas phase. A correlation between the composition and the relative volatility can be thereby found. The composition to obtain the desired relative volatility can be found from this correlation.

In each of the azeotropic composition and the azeotropic-like composition of 1233yd(E) and water, a content ratio of water with respect to a sum total of a content of 1233yd(E) and a content of water is preferably 0.001 to 5 mass %. The relative volatility is likely to fall within the range of 1.00±0.20 and the boiling point is likely to be about 40 to 48° C. as long as the content ratio of water falls within the above-stated range. The ratio is more preferably 0.01 to 2.5 mass %, further preferably 0.05 to 2 mass %, and particularly preferably 0.1 to 2 mass % in terms of making the relative volatility close to 1.00 and lowering the boiling point.

Next, a distillation composition is explained.

The distillation composition contains 1233yd(Z), 1233yd (E) and water. The distillation composition may be prepared by adding at least one kind selected from 1233yd(E) and water to a composition containing at least one kind selected from 1233yd(E) and water, and 1233yd(Z) according to need.

It is possible to obtain 1233yd through a method, for example, disclosed in International Publication No. 1994/14737. That is, 1233yd can be obtained as a by-product when 1,1,2,2,3-pentafluoropropane (HCFC-245ca) is produced by supplying 1-chloro-2,2,3,3-tetrafluoropropane (HCFC-244ca) and hydrogen fluoride in the presence of a chromium hydroxide catalyst.

It is possible to obtain 1233yd by, for example, a dehydrofluorination reaction of HCFC-244ca. The reaction can be carried out by using, for example, potassium hydroxide, sodium hydroxide, and the like as a reactant, at the temperature of 40 to 80° C.

1233yd obtained by these production methods is generally a mixture of 1233yd(Z) and 1233yd(E), and there is a case when water is mixed in during a production process. That is, a reaction composition containing at least one kind selected from 1233yd(Z), 1233yd(E) and water is obtained through the production method. The reaction composition obtained through the method may be used as the distillation composition as it is, or a composition which is prepared by adding at least one kind selected from 1233yd(E) and water in accordance with the contents of water and 1233yd(E) contained in the reaction composition may be used as the distillation composition.

The reaction composition can be classified as described below. That is, the classification can be made into a reaction composition (first reaction composition) which contains 1233yd(Z) and water, and does not contain 1233yd(E), a reaction composition (second reaction composition) which contains 1233yd(Z) and 1233yd(E), and does not contain water, and a reaction composition (third reaction composition) which contains 1233yd(Z), 1233yd(E) and water.

In a case of the first reaction composition, that is, 1233yd(Z) and water are contained and 1233yd(E) is not contained, the distillation composition can be obtained by adding 1233yd(E). The azeotropic composition or the azeotropic-like composition of 1233yd(E) and water can be formed by adding 1233yd(E).

In a case of the second reaction composition, that is, 1233yd(Z) and 1233yd(E) are contained and water is not contained, the distillation composition can be obtained by adding water. The azeotropic composition or the azeotropic-like composition of 1233yd(E) and water can be formed by adding water.

In a case of the third reaction composition, that is, 1233yd(Z), water and 1233yd(E) are contained, it can be used as the distillation composition as it is. Note that at least one kind selected from 1233yd(E) and water can be added to the third reaction composition in accordance with the contents of water and 1233yd(E).

A content of 1233yd(Z) in the distillation composition used in this embodiment is preferably 50 mass % or more with respect to a total amount of the distillation composition, more preferably 80 mass % or more, and further preferably 90 mass % or more. It is possible to efficiently remove 1233yd(E) and water if the content of 1233yd(Z) is the above-stated lower limit value or more.

Respective contents of water and 1233yd(E) in the distillation composition are not necessarily limited. The azeotropic composition or the azeotropic-like composition can be formed from water and 1233yd(E) owing to the water and 1233yd(E) contained in the distillation composition.

It is preferable that all of 1233yd(E) and water contained in the distillation composition are efficiently removed from the distillation composition by forming the azeotropic composition or the azeotropic-like composition. In this context, the content ratio of water with respect to a sum total of the content of 1233yd(E) and the content of water is preferably 0.001 to 5 mass %, more preferably 0.01 to 2.5 mass %, further preferably 0.05 to 2 mass %, and particularly preferably 0.1 to 2 mass % in the distillation composition.

The ratio of water can be adjusted by adding 1233yd(E) or water. For example, when the ratio of water is small, the ratio of water can be increased by adding water. When the ratio of water is large, the ratio of water can be decreased by adding 1233yd(E).

The distillation composition may contain components other than 1233yd(Z), 1233yd(E) and water. Examples of the components other than 1233yd(Z), 1233yd(E) and water include a production raw material of 1233yd(Z), by-products generated in addition to 1233yd(Z) and 1233yd(E), and the like. Concretely, the examples of the components other than 1233yd(Z), 1233yd(E) and water include HCFC-244ca, 1-chloro-3,3-difluoro-1-propyne, 1,1,2,2,3-pentafluoropropane, 2,3,3-trifluoro-1-propene, 1,2,3,3-tetrafluoro-1-propene, alcohol such as tetrafluoropropanol and methanol, and the like. The components other than 1233yd(Z), 1233yd(E) and water are preferably 30 mass % or less, and more preferably 10 mass % or less with respect to a total amount of the distillation composition in terms of increasing the recovery ratio of 1233yd(Z). In particular, since alcohol such as tetrafluoropropanol and methanol has a possibility of obstructing the formation of the azeotropic component of 1233yd(E) and water, a compound of these is preferably 5 mass % or less, and more preferably 1 mass % or less with respect to the total amount of the distillation composition when the compound is contained.

Next, distillation is explained.

In the method for producing 1233yd(Z) of this embodiment, distillation is carried out by using the distillation composition containing 1233yd(Z), 1233yd(E) and water. It is possible to form the azeotropic composition or the azeotropic-like composition of 1233yd(E) and water by making 1233yd(E) and water coexist in the distillation composition.

Since the boiling point of the azeotropic composition or the azeotropic-like composition of 1233yd(E) and water is about 40 to 48° C. where the boiling point of 1233yd(Z) is about 54° C., it is possible to remove at least a part of the azeotropic composition or the azeotropic-like composition of 1233yd(E) and water from the distillation composition by distilling the distillation composition. As a result, a composition where the contents of 1233ye(E) and water are reduced, that is, 1233yd(Z) with high purity can be obtained.

A publicly-known distillation apparatus can be used as a distillation apparatus as long as it is possible to remove at least a part of the azeotropic composition or the azeotropic-like composition of 1233yd(E) and water from the distillation composition.

FIG. 1 illustrates an example of the distillation apparatus.

A distillation apparatus 10 includes, for example, a distillation column 11, where a pipe 12 supplying the distillation composition, a pipe 13 taking out a distillate from a column top of the distillation column 11, and a pipe 14 taking out a bottom product from a column bottom of the distillation column 11 are connected to the distillation column 11. The distillation apparatus 10 may be either a batch type or a continuous type. The distillation column 11 may be either a hollow type or a multiplate type.

In the distillation apparatus 10 as stated above, for example, a distillate containing the azeotropic composition or the azeotropic-like composition of 1233yd(E) and water can be obtained from the column top, and a bottom product containing 1233yd(Z) can be obtained from the column bottom.

When excessive 1233yd(E) or water which exceeds the composition range of the azeotropic composition or the azeotropic-like composition of 1233yd(E) and water is contained in the distillation composition, the excessive 1233yd(E) or water may be contained in, for example, the bottom product from the column bottom.

In a case of the multiplate distillation column 10, the distillation composition is generally supplied to a middle plate of the multiplate distillation column 10. In this case, the distillate containing the azeotropic composition or the azeotropic-like composition of 1233yd(E) and water can be obtained from upper-side plates than the plate where the distillation composition is supplied. The bottom product containing 1233yd(Z) can be obtained from lower-side plates than the plate where the distillation composition is supplied.

A pressure at the distillation time is preferably 0.1 to 1.0 MPa in absolute pressure. When the pressure is set in the range, a column top temperature of the distillation column is preferably 40 to 80° C. By setting the pressure at the distillation time and the column top temperature of the distillation column in the above-stated ranges, at least a part of the azeotropic composition or the azeotropic-like composition of 1233yd(E) and water can be efficiently removed from the distillation composition.

For example, when the pressure at the distillation time is 0.1 MPa in absolute pressure, the column top temperature of the distillation column is preferably 40° C. or more, more preferably 43° C. or more, and further preferably 45° C. or more in terms of increasing a recovery amount of the distillate containing the azeotropic composition or the azeotropic-like composition of 1233yd(E) and water. The column top temperature is preferably 55° C. or less, more preferably 52° C. or less, further preferably 50° C. or less, and the most preferably 48° C. or less in terms of decreasing a ratio of 1233yd(Z) contained in the distillate.

It is possible to carry out the distillation again while using the bottom product containing 1233yd(Z) as the distillation composition. When 1233yd(E) and water are contained in the bottom product, 1233yd(E) and water can be separated by carrying out the distillation, and the bottom product where the purity of 1233yd(Z) is further increased can be obtained.

The distillate where the ratio of 1233yd(E) and water is increased can be obtained by carrying out the distillation again while using the distillate containing 1233yd(E) as the distillation composition. Besides, 1233yd(E) with high purity can be obtained by dehydrating the obtained distillate through a later-described method or the like.

According to the method for producing 1233yd(Z) of this embodiment, a recovery ratio of the bottom product can be set to, for example, 83% or more by carrying out the distillation. The recovery ratio of the bottom product is preferably 84% or more, and more preferably 85% or more. Here, the recovery ratio of the bottom product [%] is calculated by the following expression from a supply amount of the distillation composition and a recovery amount of the bottom product.

Recover ratio of bottom product [%]=(recovery amount of bottom product)/(supply amount of distillation composition)×100

According to the method for producing 1233yd(Z) of this embodiment, the recovery ratio of 1233yd(Z) in the bottom product can be set to, for example, 85% or more by carrying out the distillation. The recovery ratio of 1233yd(Z) in the bottom product is preferably 90% or more, and more preferably 95% or more. Here, the recovery ratio of 1233yd(Z) in the bottom product [%] is calculated by the following expression from a supply amount of 1233yd(Z) in the distillation composition and a recovery amount of 1233yd(Z) in the bottom product.

Recovery ratio of 1233yd(Z) in bottom product [%]=(recovery amount of 1233yd(Z) in bottom product)/(supply amount of 1233yd(Z) in distillation composition)×100

According to such distillation, it is possible to set a content ratio of 1233yd(Z) (purity of 1233yd(Z)) with respect to a sum total of contents of 1233yd(Z), 1233yd(E) and water in the bottom product to be, for example, 80 mass % or more. The ratio is preferably 90 mass % or more, more preferably 93 mass % or more, further preferably 95 mass % or more, and the most preferably 98 mass % or more.

By bringing the bottom product obtained by the distillation into contact with a solid absorbent, the content of water in the bottom product can be decreased. An example of the solid absorbent includes, for example, silica. Silica is a substance mainly having a chemical composition of $SiO_2$. Examples of silica include porous synthetic silica gel, mesoporous silica, silica alumina, and the like. One kind of silica may be used independently, or two or more kinds may be used together. A form of silica is not particularly limited, and may be a powder form, a fine-particle form, a granular form, a thin-film form, and the like.

EXAMPLES

Hereinafter, the present invention is explained in detail by way of examples. It should be noted that the present invention is not limited by these examples.

Example 1

A multiplate distillation column having a theoretical plate number of 50 was prepared as the distillation column. The distillation composition was supplied with a supply amount of 1.0 kg/h from a part of a 40th plate from the column top of the distillation column. As listed in Table 1, 0.8800 kg/h of 1233yd(Z), 0.0050 kg/h of water, and 0.1150 kg/h of 1233yd(E) were supplied as the distillation composition. After that, an operating pressure was set to the atmospheric pressure, the column top temperature was set to 45.5° C. and continuous distillation was carried out.

During the distillation, a distillate was pulled out from a column top, and a bottom product was pulled out from a column bottom. A recovery amount of water was found by using the Karl Fischer moisture meter, and recovery amounts of 1233yd(Z) and 1233yd(E) were found by using gas chromatography regarding the distillate and the bottom product. Besides, a recovery ratio (recovery amount/supply amount) was calculated from the supply amount and the recovery amount.

Supply amounts of the distillation composition are listed and recovery amounts and recovery ratios of the distillate and the bottom product are respectively listed in Table 1. Compositions of the distillation composition, the distillate, and the bottom product and a ratio of water in 1233yd(E) and water are listed in Table 2.

The composition of the distillation composition can be found from the supply amount of each component. The compositions of the distillate and the bottom product can be found from the recovery amount of each component. The ratio of water in 1233yd(E) and water can be found from the supply amount or the recovery amount of 1233yd(E) and water.

TABLE 1

|  | Distillation composition | Distillate | | Bottom product | |
| --- | --- | --- | --- | --- | --- |
|  | Supply amount [kg/h] | Recovery amount [kg/h] | Recovery ratio [%] | Recovery amount [kg/h] | Recovery ratio [%] |
| 1233yd(Z) | 0.8800 | 0.0300 | 3.4 | 0.8500 | 96.6 |
| Water | 0.0050 | 0.0049 | 98.0 | 0.0001 | 2.0 |
| 1233yd(E) | 0.1150 | 0.1110 | 96.5 | 0.0040 | 3.5 |
| Total | 1.0000 | 0.1459 | 14.6 | 0.8541 | 85.4 |

TABLE 2

|  | Distillation composition | Distillate | Bottom product |
|---|---|---|---|
| Composition [mass %] 1233yd(Z) | 88.00 | 20.56 | 99.52 |
| Water | 0.50 | 3.36 | 0.01 |
| 1233yd(E) | 11.50 | 76.08 | 0.47 |
| Ratio of water [mass %] *1 | 4.17 | 4.23 | 2.44 |

*1: A content ratio of water with respect to a sum total of a content of 1233yd(E) and a content of water.

As it is clear from Tables 1, 2, the recovery ratio of the bottom product can be set to 83 mass % or more, and a content ratio of 1233yd(Z) in the bottom product can be set to 85 mass % or more by using the distillation composition containing 1233yd(Z), 1233yd(E) and water.

Example 2

As listed in Table 3, distillation and measurement were carried out as same as Example 1 except that the supply amount of each component in the distillation composition was changed and the column top temperature was set to 47.5° C. Recovery amounts and recovers ratios of the distillate and the bottom product are respectively listed in Table 3. The compositions of the distillation composition, the distillate, and the bottom product, and the ratio of water in 1233yd(E) and water are respectively listed in Table 4.

TABLE 3

|  | Distillation composition | Distillate | | Bottom product | |
|---|---|---|---|---|---|
|  | Supply amount [kg/h] | Recovery amount [kg/h] | Recovery ratio [%] | Recovery amount [kg/h] | Recovery ratio [%] |
| 1233yd(Z) | 0.8800 | 0.0300 | 3.4 | 0.8500 | 96.6 |
| Water | 0.0005 | 0.0005 | 100.0 | 0.0000 | 0.0 |
| 1233yd(E) | 0.1195 | 0.1170 | 97.9 | 0.0025 | 2.1 |
| Total | 1.0000 | 0.1475 | 14.7 | 0.8525 | 85.3 |

TABLE 4

|  | Distillation composition | Distillate | Bottom product |
|---|---|---|---|
| Composition [mass %] 1233yd(Z) | 88.00 | 20.34 | 99.71 |
| Water | 0.05 | 0.33 | 0.00 |
| 1233yd(E) | 11.95 | 79.33 | 0.29 |
| Ratio of water [mass %] *1 | 0.42 | 0.42 | 0.00 |

*1: A content ratio of water with respect to a sum total of a content of 1233yd(E) and a content of water.

As it is clear from Tables 3, 4, the recovery ratio of the bottom product can be set to 83 mass % or more, and the content ratio of 1233yd(Z) in the bottom product can be set to 85 mass % or more by using the distillation composition containing 1233yd(Z), 1233yd(E) and water.

Example 3

As listed in Table 5, distillation and measurement were carried out as same as Example 1 except that the supply amount of each component in the distillation composition was changed and the column top temperature was set to 51.5° C. Recovery amounts and recovers ratios of the distillate and the bottom product are respectively listed in Table 5. The compositions of the distillation composition, the distillate, and the bottom product, and the ratio of water in 1233yd(E) and water are respectively listed in Table 6.

TABLE 5

|  | Distillation composition | Distillate | | Bottom product | |
|---|---|---|---|---|---|
|  | Supply amount [kg/h] | Recovery amount [kg/h] | Recovery ratio [%] | Recovery amount [kg/h] | Recovery ratio [%] |
| 1233yd(Z) | 0.9850 | 0.1350 | 13.7 | 0.8500 | 86.3 |
| Water | 0.0050 | 0.0049 | 98.0 | 0.0001 | 2.0 |
| 1233yd(E) | 0.0100 | 0.0100 | 100.0 | 0.0000 | 0.0 |
| Total | 1.0000 | 0.1499 | 15.0 | 0.8501 | 85.0 |

TABLE 6

|  | Distillation composition | Distillate | Bottom product |
|---|---|---|---|
| Composition [mass %] 1233yd(Z) | 98.50 | 90.06 | 99.99 |
| Water | 0.50 | 3.27 | 0.01 |
| 1233yd(E) | 1.00 | 6.67 | 0.00 |
| Ratio of water [mass %] *1 | 33.33 | 32.89 | 100.00 |

*1: A content ratio of water with respect to a sum total of a content of 1233yd(E) and a content of water.

As it is clear from Tables 5, 6, the recovery ratio of the bottom product can be set to 83 mass % or more, and the content ratio of 1233yd(Z) in the bottom product can be set to 85 mass % or more by using the distillation composition containing 1233yd(Z), 1233yd(E) and water.

Example 4

As listed in Table 7, distillation and measurement were carried out as same as Example 1 except that the supply amount of each component in the distillation composition was changed. The distillation composition used in Example 4 was obtained by bringing 1-chloro-2,2,3,3-tetrafluoropropane into contact with aqueous potassium hydroxide solution at 50° C. to cause a dehydrofluorination reaction. As a result of analyzation of a crude liquid after the dehydrofluorination reaction, there were contained unreacted HCFC-244ca, 1-chloro-3,3-difluoropropyne where 1233yd was further subjected to the dehydrofluorination reaction, a compound represented by a molecular formula CHCl=C(CHF$_2$)OCH$_2$CF$_2$CHF$_2$ where tetrafluoropropanol (TFPO) was added to 1233yd and the dehydrofluorination reaction was further carried out or TFPO was added to 1-chloro-3,3-difluoropropyne (hereinafter, it is denoted by 1233yd-TFPO adduct) as by-products in addition to 1233yd(Z), 1233yd(E).

Recovery amounts and recovery ratios of the distillate and the bottom product are respectively listed in Table 7. The compositions of the distillation composition, the distillate, and the bottom product, and the ratio of water in 1233yd(E) and water are respectively listed in Table 8.

TABLE 7

| Distillation composition | | Distillate | | Bottom product | |
|---|---|---|---|---|---|
| | Supply amount [kg/h] | Recovery amount [kg/h] | Recovery ratio [%] | Recovery amount [kg/h] | Recovery ratio [%] |
| 1233yd(Z) | 0.7970 | 0.0167 | 2.1 | 0.7802 | 97.90 |
| Water | 0.0060 | 0.0059 | 98.3 | 0.0001 | 1.70 |
| 1233yd(E) | 0.0778 | 0.0745 | 95.8 | 0.0033 | 4.20 |
| 244ca | 0.0596 | 0.0332 | 55.6 | 0.0265 | 44.40 |
| 1-chloro-3,3-difluoro-propyne | 0.0398 | 0.0390 | 98.1 | 0.0008 | 1.90 |
| 1233yd-TFPO adducts | 0.0199 | 0.0001 | 0.5 | 0.0198 | 99.50 |
| Total | 1.0000 | 0.1694 | 16.9 | 0.8306 | 83.1 |

TABLE 8

| | Distillation composition | Distillate | Bottom product |
|---|---|---|---|
| Composition [mass %] 1233yd(Z) | 79.90 | 9.88 | 93.93 |
| Water | 0.60 | 3.48 | 0.01 |
| 1233yd(E) | 7.78 | 43.98 | 0.39 |
| 244ca | 5.96 | 19.57 | 3.19 |
| 1-chloro-3,3-difluoropropyne | 3.98 | 23.03 | 0.09 |
| Water | 1.99 | 0.06 | 2.38 |
| Ratio of water [mass %] *1 | 7.16 | 7.33 | 2.50 |

*1: A content ratio of water with respect to a sum total of a content of 1233yd(E) and a content of water.

As it is clear from Tables 7, 8, the recovery ratio of the bottom product can be set to 83 mass % or more, and the content ratio of 1233yd(Z) in the bottom product can be set to 85 mass % or more by using a reaction composition obtained by subjecting 1-chloro-2,2,3,3-tetrafluoropropane to the defluorination reaction as the distillation composition.

Comparative Example 1

As listed in Table 9, distillation and measurement were carried out as same as Example 1 except that the supply amount of each component in the distillation composition was changed and the column top temperature was set to 53.0° C. Recovery amounts and recovery ratios of the distillate and the bottom product are respectively listed in Table 9. The compositions of the distillation composition, the distillate, and the bottom product, and the ratio of water in 1233yd(E) and water are respectively listed in Table 10.

TABLE 9

| Distillation composition | | Distillate | | Bottom product | |
|---|---|---|---|---|---|
| | Supply amount [kg/h] | Recovery amount [kg/h] | Recovery ratio [%] | Recovery amount [kg/h] | Recovery ratio [%] |
| 1233yd(Z) | 0.9950 | 0.1870 | 18.8 | 0.8080 | 81.2 |
| Water | 0.0050 | 0.0047 | 94.0 | 0.0003 | 6.0 |
| 1233yd(E) | — | — | — | — | — |
| Total | 1.0000 | 0.1917 | 19.2 | 0.8083 | 80.8 |

TABLE 10

| | | Distillation composition | Distillate | Bottom product |
|---|---|---|---|---|
| Composition [mass %] | 1233yd(Z) | 99.50 | 97.55 | 99.96 |
| | Water | 0.50 | 2.45 | 0.04 |
| | 1233yd(E) | 0.00 | 0.00 | 0.00 |
| Ratio of water [mass %] *1 | | 100.00 | 100.00 | 100.00 |

*1: A content ratio of water with respect to a sum total of a content of 1233yd(E) and a content of water.

As it is clear from Tables 9, 10, the distillation composition of Comparative Example 1 contains 1233yd(Z) and water, and does not contain 1233yd(E). When 1233yd(E) is not contained, the recovery ratio of the bottom product decreases compared to the case when 1233yd(E) is contained. Further, it can be seen that 1233yd(Z) and water are not sufficiently separated.

According to the present invention, 1233yd(E) and water can be efficiently removed, a recovery ratio of 1233yd(Z) can be increased, and purity of 1233yd(Z) can be increased. Accordingly, it can be effectively used for various fields such as a cleaning agent, a solvent, and a refrigerant where 1233yd(Z) is used.

What is claimed is:

1. A composition, comprising:
   (Z)-1-chloro-2,3,3-trifluoro-1-propene;
   (E)-1-chloro-2,3,3-trifluoro-1-propene; and
   water,
   wherein a proportion of (Z)-1-chloro-2,3,3-trifluoro-1-propene with respect to a sum total of contents of the (Z)-1-chloro-2,3,3-trifluoro-1-propene, (E)-1-chloro-2,3,3-trifluoro-1-propene and water is 90 mass % or more.

2. The composition according to claim 1, wherein a content of water in the composition is 0.01% or less.

3. The composition according to claim 1, wherein the proportion of (Z)-1-chloro-2,3,3-trifluoro-1-propene with respect to a sum total of contents of the (Z)-1-chloro-2,3,3-trifluoro-1-propene, (E)-1-chloro-2,3,3-trifluoro-1-propene and water is 93 mass % or more.

4. The composition according to claim 1, wherein the proportion of (Z)-1-chloro-2,3,3-trifluoro-1-propene with respect to a sum total of contents of the (Z)-1-chloro-2,3,3-trifluoro-1-propene, (E)-1-chloro-2,3,3-trifluoro-1-propene and water is 95 mass % or more.

5. The composition according to claim 1, wherein the proportion of (Z)-1-chloro-2,3,3-trifluoro-1-propene with respect to a sum total of contents of the (Z)-1-chloro-2,3,3-trifluoro-1-propene, (E)-1-chloro-2,3,3-trifluoro-1-propene and water is 98 mass % or more.

* * * * *